United States Patent
Uchisasai (10) Patent No.: US 10,577,049 B2
(45) Date of Patent: Mar. 3, 2020

(54) SADDLE-TYPE VEHICLE

(71) Applicant: HONDA MOTOR CO., LTD., Minato-ku, Tokyo (JP)

(72) Inventor: Hiroaki Uchisasai, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 16/142,043

(22) Filed: Sep. 26, 2018

(65) Prior Publication Data

US 2019/0100276 A1 Apr. 4, 2019

(30) Foreign Application Priority Data

Sep. 29, 2017 (JP) ................... 2017-189773

(51) Int. Cl.
| | |
|---|---|
| *B62M 6/50* | (2010.01) |
| *B60R 25/25* | (2013.01) |
| *A42B 3/04* | (2006.01) |
| *B62H 5/08* | (2006.01) |
| *G01N 33/497* | (2006.01) |
| *G06K 9/00* | (2006.01) |

(Continued)

(52) U.S. Cl.
CPC ............. *B62M 6/50* (2013.01); *A42B 3/042* (2013.01); *A42B 3/046* (2013.01); *B60R 25/25* (2013.01); *B62H 5/08* (2013.01); *B62J 99/00* (2013.01); *G01N 33/4972* (2013.01); *G06K 9/00288* (2013.01); *G06K 9/00597* (2013.01); *H04N 5/232* (2013.01); *A42B 3/12* (2013.01); *B60R 2325/306* (2013.01); *B62J 2099/002* (2013.01); *G06T 7/73* (2017.01); *G06T 2207/30201* (2013.01); *H04N 5/76* (2013.01)

(58) Field of Classification Search
CPC .... H04W 12/06; B60R 25/04; B60R 25/1001; B60R 25/24; B60R 2325/20; B60R 2325/306; B60R 25/245; B60R 25/25; G02B 2027/0138; G02B 2027/014; G02B 2027/0178; G02B 27/017; G06F 21/32; G06K 9/00617; H04L 63/0861; B62J 2099/002
USPC .................................................... 348/148, 78
See application file for complete search history.

(56) References Cited

U.S. PATENT DOCUMENTS 9,747,500 B2 * 8/2017 Andersen ................ G06F 21/32
10,029,683 B1 * 7/2018 Ginther ................ B60W 30/09
(Continued)

FOREIGN PATENT DOCUMENTS

| EP | 1698529 | 9/2006 |
|---|---|---|
| JP | 11-043016 | 2/1999 |

(Continued)

OTHER PUBLICATIONS

Vijayan et al. "Alcohol Detection Using Smart Helmet System" Apr. 2014, 6 pages. (Year: 2014).*

(Continued)

*Primary Examiner* — Nathnael Aynalem
(74) *Attorney, Agent, or Firm* — Amin, Turocy & Watson, LLP (57) ABSTRACT

A saddle-type vehicle includes a helmet and an occupant authentication device configured to perform authentication of an occupant by a small camera (an imaging element) provided in the helmet. The occupant authentication device releases lock on the vehicle if the occupant is authenticated.

9 Claims, 7 Drawing Sheets

(51) Int. Cl.
  *B62J 99/00* (2020.01)
  *H04N 5/232* (2006.01)
  *H04N 5/76* (2006.01)
  *G06T 7/73* (2017.01)
  *A42B 3/12* (2006.01)

(56) References Cited

U.S. PATENT DOCUMENTS

| | | | |
|---|---|---|---|
| 2009/0002161 A1* | 1/2009 | Luciani | A42B 3/0466 340/568.6 |
| 2014/0111630 A1* | 4/2014 | Pires | A61B 3/113 348/78 |
| 2016/0075338 A1* | 3/2016 | Henn | B60K 28/066 340/439 |
| 2016/0274244 A1 | 9/2016 | Dhaliwal | |

FOREIGN PATENT DOCUMENTS

| | | |
|---|---|---|
| JP | 2001-303353 | 10/2001 |
| JP | 2008-214770 | 9/2008 |
| JP | 2009-226992 | 10/2009 |
| JP | 2013-203294 | 10/2013 |
| TW | 201012684 A * | 4/2010 |
| WO | 2005/110138 | 11/2005 |
| WO | 2017/163488 | 9/2017 |

OTHER PUBLICATIONS

Extended European Search Report for European Patent Application No. 18197203.5 dated Feb. 11, 2019.

Japanese Office Action for Japanese Patent Application No. 2017-189773 dated Feb. 19, 2019.

* cited by examiner

SADDLE-TYPE VEHICLE

CROSS-REFERENCE TO RELATED APPLICATION

This application is based upon and claims the benefit of priority from Japanese Patent Application No. 2017-189773 filed on Sep. 29, 2017, the contents of which are incorporated herein by reference.

BACKGROUND OF THE INVENTION

Field of the Invention

The present invention relates to a saddle-type vehicle having an occupant authentication function.

Description of the Related Art

In a saddle-type vehicle described in Japanese Laid-Open Patent Publication No. 2013-203294, an object thereof is to lock the vehicle so that the vehicle cannot travel even when a rider temporarily gets off the vehicle and unlock the vehicle by a simple operation so that the vehicle can travel.

To attain this object, the saddle-type vehicle according to Japanese Laid-Open Patent Publication No. 2013-203294 includes an ECU that outputs riding-on/getting-off information regarding a determination as to whether or not a rider is riding on the vehicle, and a mobile terminal that is detachably attached by the rider of an electric two-wheeled vehicle. The mobile terminal includes a vehicle lock control module that puts the electric two-wheeled vehicle into a locked state or an unlocked state based on the riding-on/getting-off information, a user interface that outputs operation information in accordance with an operation to put the electric two-wheeled vehicle into an unlocked state, and a display control module that displays a method of operating the user interface. Based on the operation information, it is determined whether or not an occupant riding on the vehicle is the rider of the electric two-wheeled vehicle, and the electric two-wheeled vehicle is put into an unlocked state in accordance with the determination result.

SUMMARY OF THE INVENTION

The conventional saddle-type vehicle as disclosed in Japanese Laid-Open Patent Publication No. 2013-203294 performs face authentication based on an image captured by a camera of a terminal (a mobile terminal) carried around by an occupant.

In general, in face authentication, two types of processing, "face detection" and "face matching", are mainly performed. In face detection processing, a face region is determined in the image captured by a camera function of the mobile terminal and then, by detecting face feature points, the positions of feature points of a face, such as eyes, a nose, and a mouth, are obtained. Next, the position and size of the face region are normalized by using the obtained positions of feature points, and face matching processing is then performed.

Thus, in the conventional technique, a motion of turning a face toward the screen of the mobile terminal is needed solely for the purpose of face authentication. That is, in addition to a series of normal motions for riding on the saddle-type vehicle, a motion of turning a face toward the screen of the mobile terminal is needed to perform face authentication, which is bothersome. The same is true in a case where face authentication is performed based on an image captured by a camera installed in a vehicle body, and also in this case, an additional motion of turning a face toward the screen of the camera installed in the vehicle body is needed.

Japanese Laid-Open Patent Publication No. 2013-203294 discloses that, when performing authentication of an occupant wearing a helmet, the authentication is performed based on an image of the helmet.

It goes without saying that there is a device that locks handlebars by normal locking. However, a problem exists that, if an unlocking key is lost, the lock cannot be released, or there is a concern that the lock is released by another person who obtained the unlocking key, and thus a further security improvement is needed.

The present invention has been made to solve the above-described problems, and an object thereof is to provide a saddle-type vehicle that is capable of improving security compared to a case of normal unlocking using an unlocking key, and performing authentication of an occupant during a series of normal motions for riding on the saddle-type vehicle unlike authentication performed by using an imaging element attached to a mobile terminal or a vehicle body.

According to an aspect of the present invention, there is provided a saddle-type vehicle including a helmet, and an occupant authentication device configured to perform authentication of an occupant by an imaging element provided in the helmet, and the occupant authentication device releases lock on a vehicle if the occupant is authenticated.

According to the aspect of the present invention, compared to normal release of the lock using an unlocking key, it is possible to improve security. Unlike authentication by an imaging element attached to a mobile terminal or a vehicle body, it is possible to perform authentication of the occupant during a series of normal motions of riding on a saddle-type vehicle. This makes it possible to release the lock on the vehicle promptly and easily.

Moreover, since occupant authentication is performed by making a motion of putting on the helmet, it is possible to enhance moral standards of the occupant who rides on the vehicle. In addition, it is only necessary to identify the owner of the vehicle, that is, the owner of the helmet in the occupant authentication, and there is no need to identify plural persons. Thus, it is possible to simplify an authentication system.

The above and other objects features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Hereinafter, an embodiment of a saddle-type vehicle according to the present invention will be described with reference to FIGS. 1A to 7.

Figure 1A:
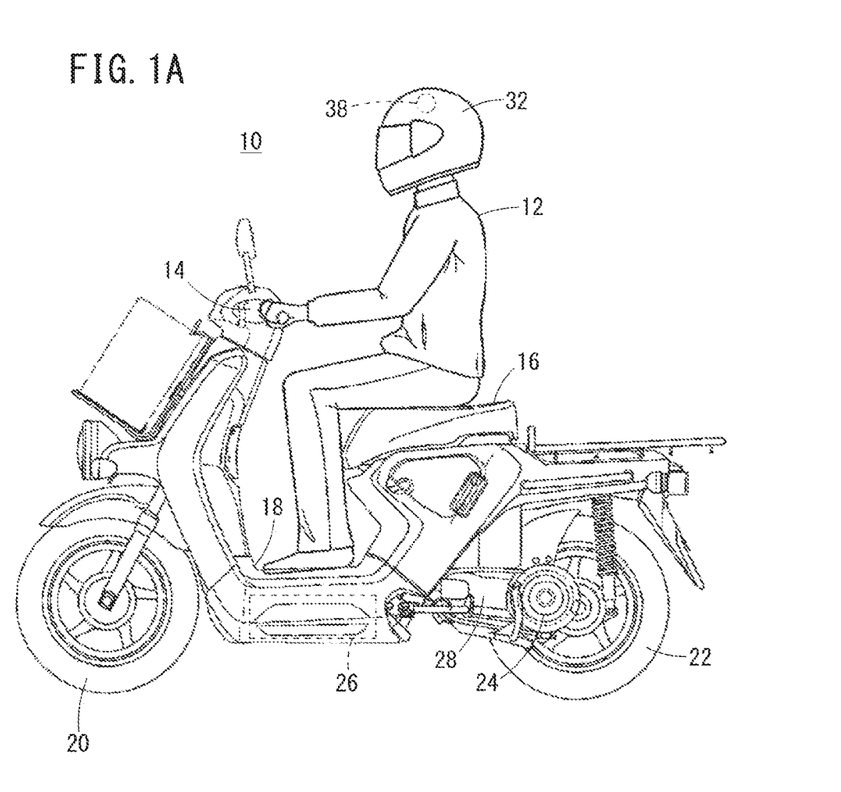
FIG. 1A is a side view depicting an example of a saddle-type vehicle according to the present embodiment.

A saddle-type vehicle (hereinafter referred to as a vehicle 10) according to the present embodiment includes steering handlebars 14 which are operated by an occupant 12, a seat 16 on which the occupant 12 sits, a floor 18 configured so that the occupant 12 can rest his/her feet thereon, a front wheel 20 which is a steered wheel, a rear wheel 22 which is a drive wheel, and an electric motor 24 which drives the rear wheel 22.

The vehicle 10 travels as a result of the electric motor 24 incorporated into a swing arm 28 being driven by electric power which is supplied from a battery 26 installed in the floor 18, for example, and rotative power generated when the electric motor 24 is driven being transferred to the rear wheel 22. The occupant 12 wearing a helmet 32 rides the vehicle 10 while operating the steering handlebars 14.

Figure 1B:
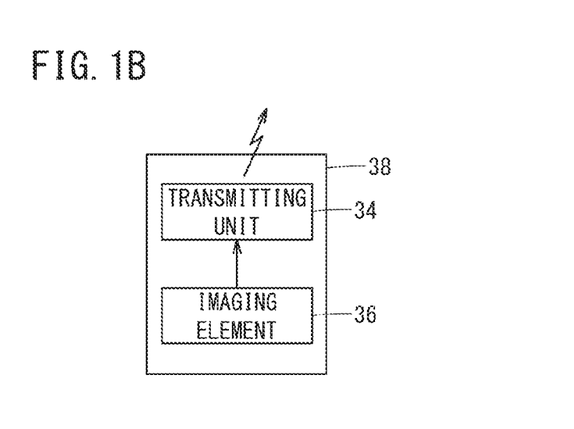
FIG. 1B is a configuration diagram depicting a small camera disposed in a helmet.
Figure 2:
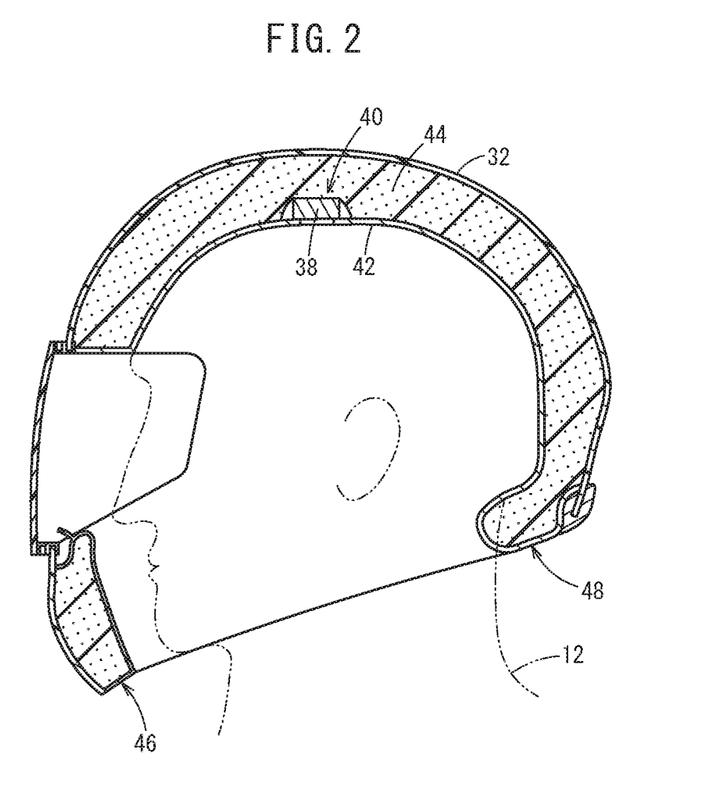
FIG. 2 is a sectional view depicting an example in which the small camera is disposed on a crown inner side of the helmet.
Figure 3A:
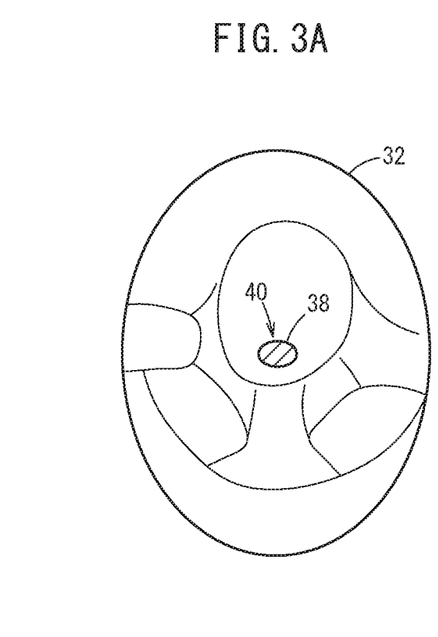
FIG. 3A is a diagram depicting the example in which the small camera is disposed on the crown inner side of the helmet, as viewed from under the helmet.

In addition, in the helmet 32, as depicted in FIG. 1B, a small camera 38 equipped with a transmitting unit 34 and an imaging element 36, for instance, is disposed. As depicted in FIGS. 2 and 3A, the small camera 38 is disposed on a crown inner side 40, for example, of the helmet 32. In particular, it is preferable to dispose the small camera 38 between an outside cover member 42 and a cushion member 44 of the helmet 32.

Figure 3B:
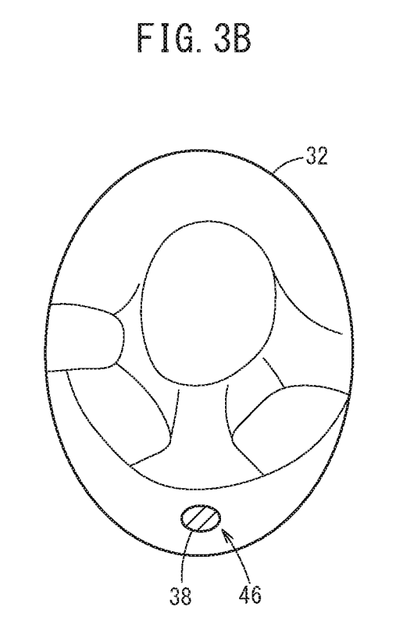
FIG. 3B is a diagram depicting an example in which the small camera is disposed at a front lower part of the helmet, as viewed from under the helmet.
Figure 3C:
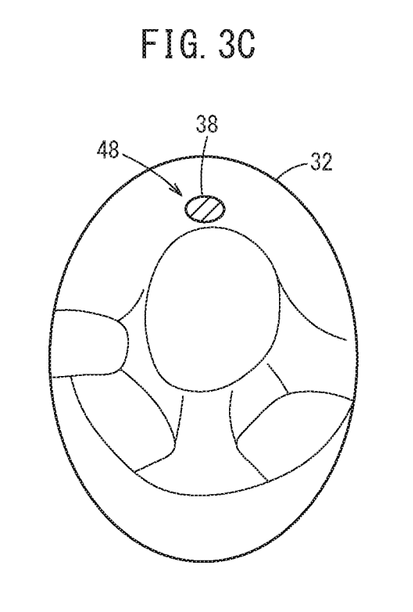
FIG. 3C is diagram depicting an example in which the small camera is disposed at a rear lower part of the helmet, as viewed from under the helmet.

Examples of the position at which the small camera 38 is disposed include a front lower part 46 of the helmet 32 as depicted in FIG. 3B and a rear lower part 48 of the helmet 32 as depicted in FIG. 3C. Also in these cases, it is preferable to dispose the small camera 38 between the outside cover member 42 and the cushion member 44 of the helmet 32.

Figure 4:
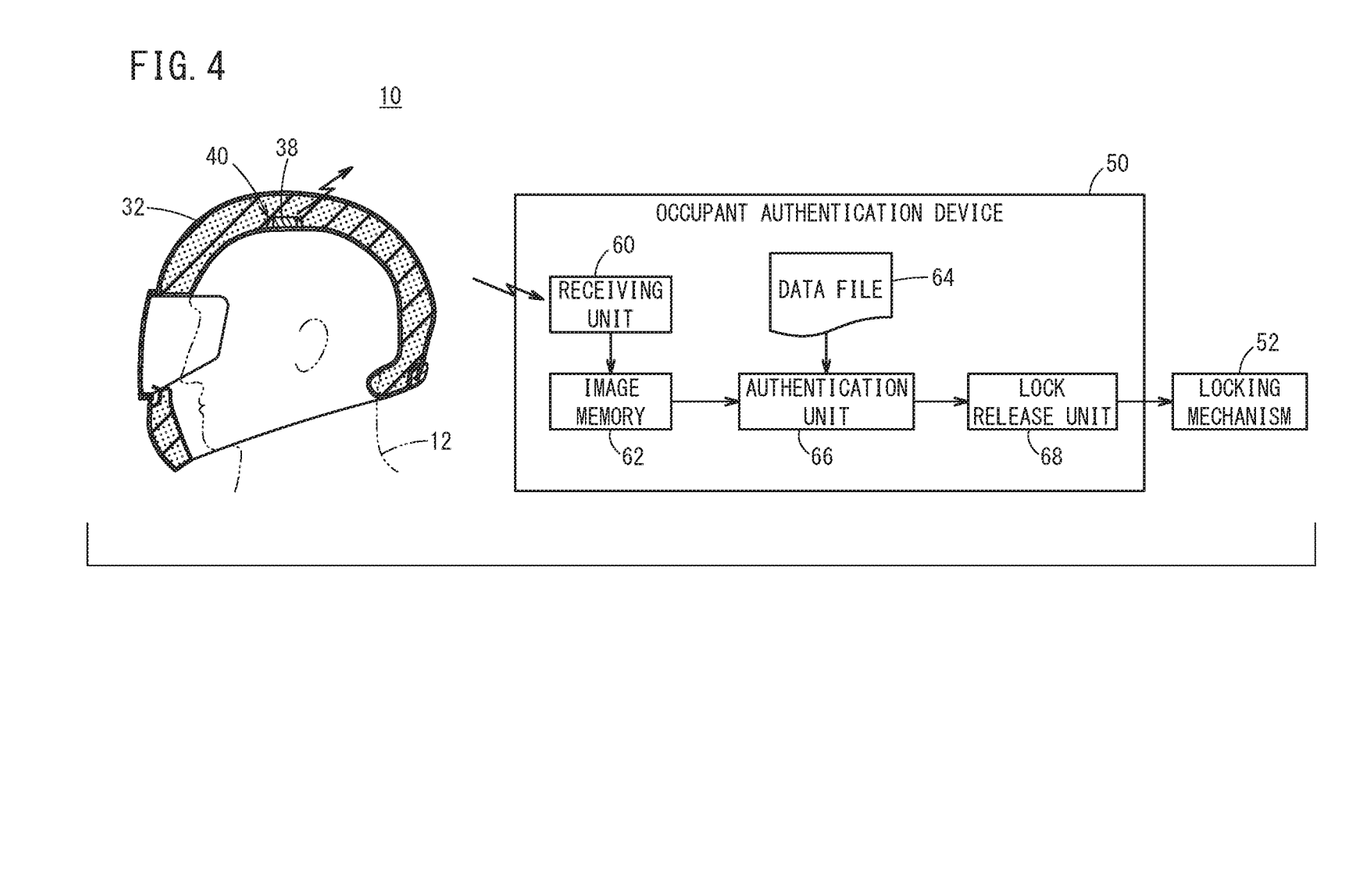
FIG. 4 is a configuration diagram depicting the configuration of the saddle-type vehicle, in particular, the helmet and an occupant authentication device.

Furthermore, in the present embodiment, as depicted in FIG. 4, an occupant authentication device 50 that differentiates the owner (the occupant 12) of the vehicle 10 from a third party other than the owner is provided. In general, the vehicle 10 includes a locking mechanism 52 (such as an electronic key system) that locks the vehicle 10. When the occupant 12 or the third party rides on the vehicle 10, if the occupant authentication device 50 authenticates the owner (the occupant 12) (affirmative authentication), the occupant authentication device 50 releases the lock by the locking mechanism 52. This allows the occupant 12 to ride the vehicle 10.

As depicted in FIG. 4, the occupant authentication device 50 includes a receiving unit 60, an image memory 62, a data file 64, an authentication unit 66, and a lock release unit 68.

The receiving unit 60 receives information transmitted from the transmitting unit 34 of the small camera 38. The image memory 62 stores the received information, that is, image information. The data file 64 stores reference data on a face and the like which is required for authentication of the occupant 12. The authentication unit 66 performs authentication of the occupant 12 by checking the received image information against the reference data from the data file 64. The authentication unit 66 outputs a lock release signal Sa if the authentication unit 66 authenticates the occupant 12. The lock release unit 68 releases the lock by the locking mechanism 52 based on the input of the lock release signal Sa from the authentication unit 66.

At least the authentication unit 66 is made up of one or more electronic circuits having, for example, one or more central processing units (CPU), a storage device, etc. The electronic circuit is also a software function section that implements a predetermined function as a result of the CPU executing a program stored in the storage device, for example. It goes without saying that the authentication unit 66 may be made up of an integrated circuit, such as a field-programmable gate array (FPGA), obtained by connecting a plurality of electronic circuits depending on a function.

Figure 5:
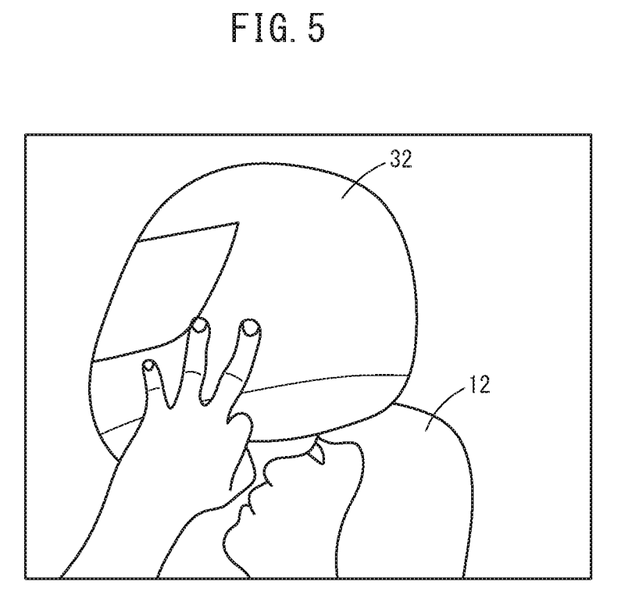
FIG. 5 is an explanatory diagram depicting an example of an occupant's motion of putting on the helmet.

When riding on the vehicle 10, as depicted in FIG. 5, the occupant 12 makes a motion of putting on the helmet 32 for safety of the occupant 12. That is, the motion of putting on the helmet 32 is made during a series of normal motions for riding on the vehicle 10. As in an example of FIG. 5, in the case that the small camera 38 is disposed on the crown inner side 40 of the helmet 32, authentication of the occupant 12 can be performed when the occupant 12 makes a motion of looking into the helmet 32 at the time of putting on the helmet 32.

That is, authentication of the occupant 12 is automatically performed when the occupant 12 performs a series of normal motions for riding on the vehicle 10, without feeling obligated to perform authentication and without consciously turning his/her face toward the camera attached to the mobile terminal or the vehicle body.

Since the helmet 32 is used as a medium for occupant authentication, a motion of putting on the helmet 32 is required for riding on the vehicle 10. This makes it possible to improve morals regarding compliance with a safety rule that the rider should wear the helmet 32 when riding on the vehicle 10. In addition, in the occupant authentication, it is only necessary to identify the owner of the vehicle 10, that is, the owner of the helmet 32, and there is no need to identify plural persons. This makes it possible to reduce the amount of data for authentication which is recorded in the data file 64, and simplify an authentication system.

Next, two modified examples (a first vehicle 10A and a second vehicle 10B) of the vehicle 10 will be described with reference to FIGS. 6 and 7.

Figure 6:
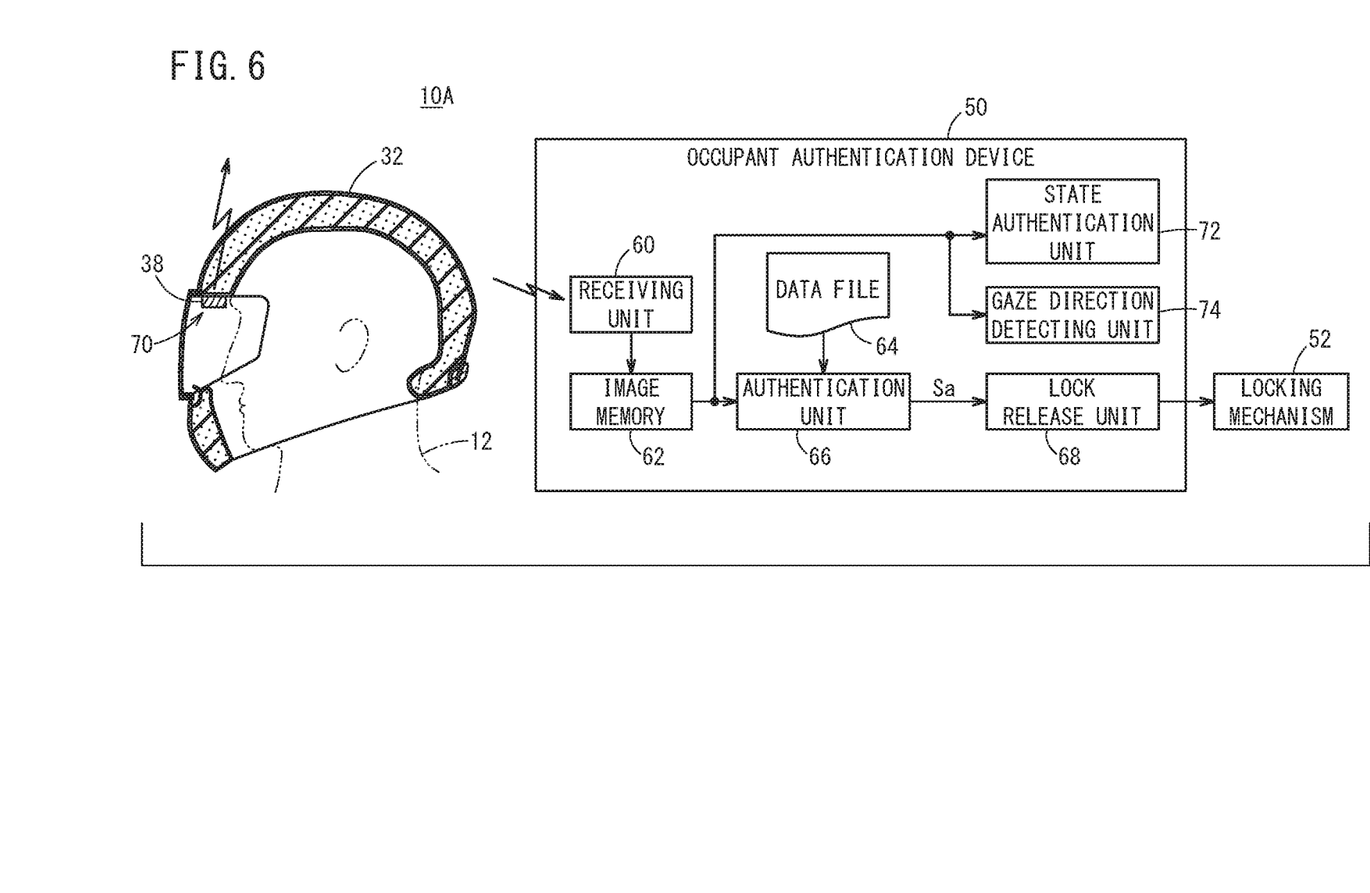
FIG. 6 is a configuration diagram depicting the configuration of a saddle-type vehicle according to a first modified example, in particular, a helmet and an occupant authentication device.

The first vehicle 10A has substantially the same configuration as the above-described vehicle 10 as depicted in FIG. 6, but differs from the vehicle 10 in that the small camera 38 is attached at a front-edge lower end 70 of the helmet 32 and that the occupant authentication device 50 includes a state authentication unit 72 and a gaze direction detecting unit 74.

The state authentication unit 72 performs authentication of a state of the occupant 12 during riding, based on an image of the occupant 12 recorded on the image memory 62. Examples of state authentication include authentication for determining whether to continue riding the vehicle. The gaze direction detecting unit 74 detects the direction of gaze of the occupant 12 during riding the vehicle, based on an image of the occupant 12 recorded on the image memory 62.

At least the authentication unit 66, the state authentication unit 72, and the gaze direction detecting unit 74 are made up of one or more electronic circuits having, for example, one or more CPUs, a storage device, and so forth. The electronic circuit is also a software function section that implements a predetermined function as a result of the CPU executing a program stored in the storage device, for example. Also in this case, the authentication unit 66, the state authentication unit 72, and the gaze direction detecting unit 74 may be made up of an integrated circuit, such as a field-programmable gate array (FPGA), obtained by connecting a plurality of electronic circuits depending on a function.

By installing the small camera 38 at the front-edge lower end 70 of the helmet 32, an image of the occupant 12 after having put on the helmet 32 is captured and recorded on the image memory 62 of the occupant authentication device 50. In this case, since the positions of the occupant 12 and the small camera 38 change little, the positional relationship between the eyes of the occupant 12 and the front edge of the helmet 32 changes little. Therefore, the authentication unit 66 can perform checking against the reference data from the data file 64 with high accuracy, and thus it is possible to perform more accurate authentication of the occupant 12.

Figure 7:
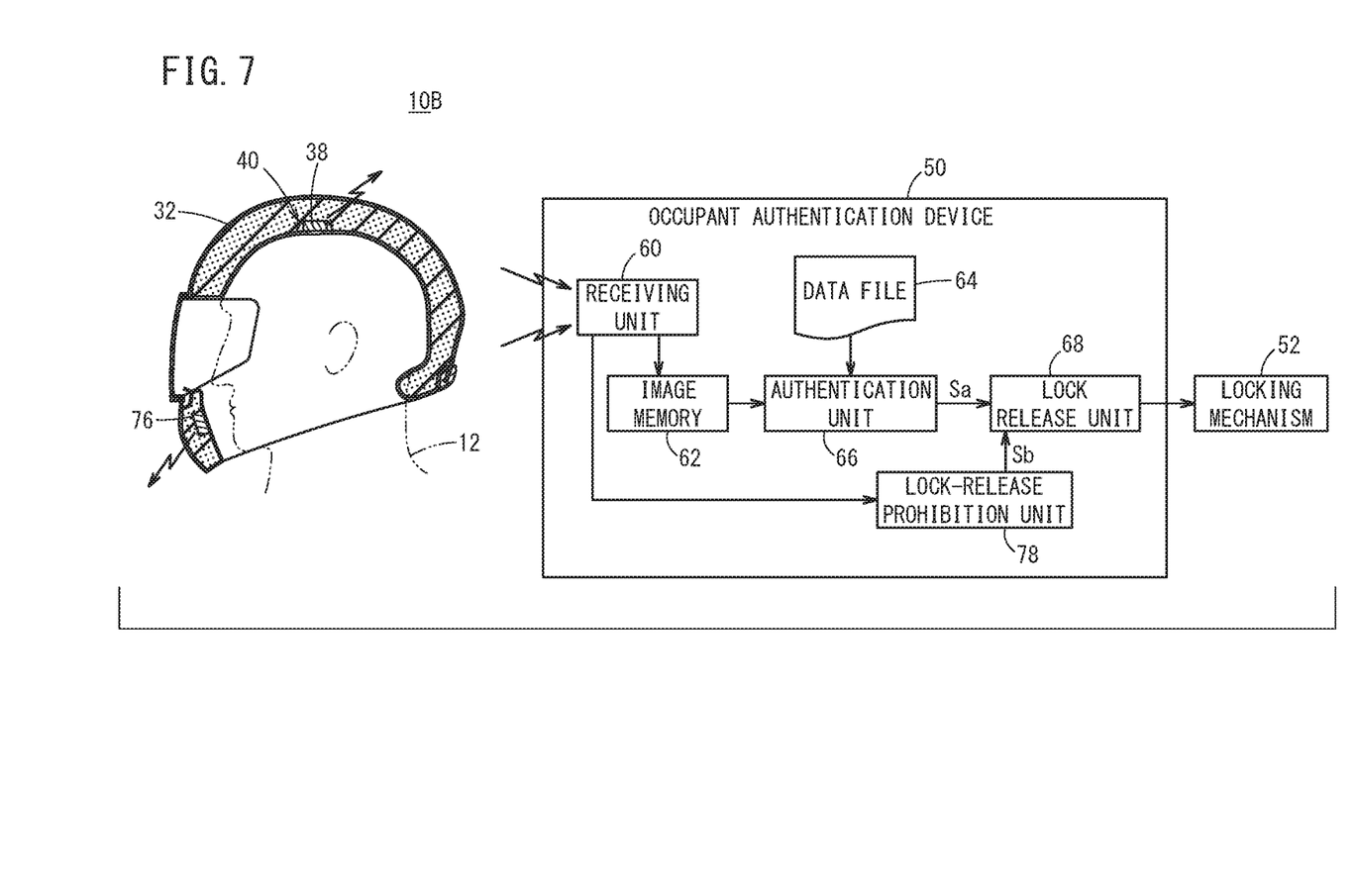
FIG. 7 is a configuration diagram depicting the configuration of a saddle-type vehicle according to a second modified example, in particular, a helmet and an occupant authentication device.

The second vehicle 10B has substantially the same configuration as the above-described vehicle 10 as depicted in FIG. 7, but differs from the vehicle 10 in that, in addition to the small camera 38, a breath sensor 76 is disposed in the helmet 32 and that a lock-release prohibition unit 78 is provided. In FIG. 7, an example in which the breath sensor 76 is disposed at a position that faces the mouth of the occupant 12, inside the helmet 32 is depicted, but the position is not limited thereto.

The breath sensor 76 outputs a measurement value indicating the concentration of alcohol in the breath of the occupant 12. The measurement value from the breath sensor 76 is supplied to the lock-release prohibition unit 78 via the receiving unit 60. If the input measurement value from the breath sensor 76 is more than or equal to a reference value, the lock-release prohibition unit 78 outputs a lock-release prohibition signal Sb to the lock release unit 68. Examples of the reference value include a reference value for drunk driving.

Even when the lock release signal Sa is supplied from the authentication unit 66, the lock release unit 68 does not release the lock by the locking mechanism 52 if the lock release unit 68 is supplied with the lock-release prohibition signal Sb from the lock-release prohibition unit 78.

The above-described vehicles are examples obtained by applying the present invention to an electric two-wheeled vehicle which is driven by the electric motor 24; in addition thereto, the present invention can also be applied to a motorcycle which is driven by a power unit with an engine and a hybrid vehicle which is driven by a power unit with an engine and an electric motor.

[Invention which is Obtained by Embodiment]

An invention which can be obtained by the embodiment and modified examples described above will be described below.

The saddle-type vehicle according to the present embodiment includes the helmet 32 and the occupant authentication device 50 configured to perform authentication of the occupant 12 by the imaging element 36 provided in the helmet 32, and the occupant authentication device 50 releases lock on the vehicle 10 if the occupant 12 is authenticated.

Compared to normal release of the lock using an unlocking key, it is possible to improve security. Unlike authentication by the imaging element 36 attached to a mobile terminal or a vehicle body, it is possible to perform authentication of the occupant 12 during a series of normal motions of riding on the vehicle 10. This makes it possible to release the lock on the vehicle 10 promptly and easily.

Moreover, since occupant authentication is performed by making a motion of putting on the helmet 32, it is possible to enhance moral standards of the occupant 12 who rides on the vehicle 10. In addition, it is only necessary to identify the owner of the vehicle 10, that is, the owner of the helmet 32 in the occupant authentication, and there is no need to identify plural persons. Thus, it is possible to simplify an authentication system.

In the present embodiment, the imaging element 36 is disposed on the crown inner side 40 of the helmet 32. By disposing the imaging element 36 on the crown inner side 40 of the helmet 32, authentication of the occupant 12 can be performed when the occupant 12 makes a motion of looking into the helmet 32 at the time of putting on the helmet 32. By disposing the imaging element 36 in the central part of the crown inner side 40 of the helmet 32, it is also possible to improve the accuracy of authentication.

In the present embodiment, the imaging element 36 is disposed at the front lower part 46 or the rear lower part 48 of the helmet 32. Since the imaging element 36 is positioned so as to be closest to the rider when the occupant 12 turns the helmet 32 upside down at the time of putting on the helmet 32, authentication accuracy is increased.

In the present embodiment, the imaging element 36 is disposed between the outside cover member 42 and the cushion member 44. With this configuration, the imaging element 36 is placed between the outside cover member 42 and the cushion member 44, and thus it is possible to prevent the imaging element 36 from making contact from the outside, and lessen impact from the head of the occupant 12.

In the present embodiment, the imaging element 36 is provided at the front-edge lower end 70 of the helmet 32, and the occupant authentication device 50 performs authentication of the occupant 12 by recognizing an eye of the occupant 12.

Since the positional relationship between the front edge of the helmet 32 and the eyes of the occupant 12 after having put on the helmet 32 changes little, it is possible to perform more accurate authentication of the occupant 12. Moreover, the imaging element 36 can be used in combination with the functions of authentication of the state of the occupant 12 during riding the vehicle and detection of the gaze direction of the occupant 12 during riding the vehicle, and thus it is possible to set a plurality of functions at low cost.

In the present embodiment, in the helmet 32, the breath sensor 76 is further disposed, and the occupant authentication device 50 prohibits release of the lock if the concentration of alcohol in the breath is more than or equal to a reference value which is set in advance. This makes it possible to avoid in advance drunk driving of the occupant 12, for example.

It goes without saying that this invention is not limited to the embodiment described above and any change can be made thereto within the scope of this invention.

That is, although in the above-described embodiment, an example is given in which the small camera 38 is provided in the helmet 32, the small camera 38 may be provided on the outside (such as an outer surface) of the helmet 32.

Moreover, the small camera 38 may be provided with a thermometer. This makes it possible to measure the body temperature of the occupant 12 through the head of the occupant 12, making it also possible to keep track of the health condition of the occupant 12.

When a helmet remover is placed inside the helmet 32, since the helmet remover covers the entire head of the occupant 12, an electrode for measuring brain waves may be attached to the helmet remover. This makes it possible to keep track of the state of mind of the occupant 12 before riding the vehicle or during riding the vehicle, for example.

What is claimed is:

1. A saddle-type vehicle comprising:
   a helmet; and
   an occupant authentication device comprising:
      at least one storage device that stores an executable program;
      at least one central processing unit configured to execute the executable program, wherein execution of the executable program causes the occupant authentication device to
         capture image information of an occupant's face using an imaging element located in an inner crown of the helmet as the occupant is looking into the helmet; and
         perform authentication of an occupant by checking the image information against a data file that stores reference data on the occupant's face,
   wherein the occupant authentication device releases a lock on a vehicle if the occupant is authenticated.

2. The saddle-type vehicle according to claim 1, wherein the imaging element is disposed between an outside cover member and a cushion member.

3. The saddle-type vehicle according to claim 1, wherein the occupant authentication device performs authentication of the occupant by recognizing an eye of the occupant.

4. The saddle-type vehicle according to claim 1, further comprising a breath sensor disposed in the helmet,
   wherein the occupant authentication device prohibits release of the lock in response to a determination that a concentration of alcohol in breath detected by the breath sensor is greater than or equal to a reference value.

5. The saddle-type vehicle according to claim 1, further comprising:
   a transmitting unit configured to transmit image information captured by the imaging element;
   an image memory configured to store the image information received by the receiving unit;
   a data file that stores reference data representing a face;
   an authentication unit configured to perform authentication of the occupant by checking the image information against the reference data; and
   a lock release unit configured to release the lock on the vehicle in response to a determination by the authentication unit authenticates that the image information corresponds to the reference data.

6. The saddle-type vehicle according to claim 5, further comprising:
   a state authentication unit configured to perform authentication of a state of the occupant during riding the vehicle based on an image of the occupant recorded on the image memory, wherein
   the authentication of the state is at least authentication to determine whether to continue riding the vehicle.

7. The saddle-type vehicle according to claim 5, further comprising:
   a gaze direction detecting unit configured to detect a direction of a gaze of the occupant during riding of the vehicle based on an image of the occupant recorded on the image memory.

8. The saddle-type vehicle according to claim 1, further comprising a thermometer configured to measure a temperature of a wearer of the helmet.

9. The saddle-type vehicle according to claim 1, further comprising an electrode mounted in the helmet and configured to track a state of mind of the occupant based on brain waves measured by the electrode.

* * * * *